United States Patent [19]

Chernoff

[11] Patent Number: 4,895,572
[45] Date of Patent: Jan. 23, 1990

[54] INTERLOCKING FEMORAL PROSTHESIS DEVICE

[76] Inventor: Ira Chernoff, 515 E. 72nd St., Apt. 19A, New York, N.Y. 10021

[21] Appl. No.: 276,124

[22] Filed: Nov. 25, 1988

[51] Int. Cl.⁴ .......................... A61F 2/32; A61F 5/04
[52] U.S. Cl. ....................................... 623/23; 606/64
[58] Field of Search ........................ 623/16, 18, 23; 128/92 YY

[56] References Cited

U.S. PATENT DOCUMENTS

| | | | |
|---|---|---|---|
| 3,922,726 | 12/1975 | Trentani et al. | 623/22 |
| 3,995,323 | 12/1976 | Shersher | 623/23 |
| 4,080,666 | 3/1978 | Fixel | 128/92 YY |
| 4,608,052 | 8/1986 | Van Kampen et al. | 623/22 |
| 4,705,027 | 11/1987 | Klaue | 128/92 YY |
| 4,776,330 | 10/1988 | Chapmann et al. | 128/92 YY |

FOREIGN PATENT DOCUMENTS

| | | | |
|---|---|---|---|
| 0118778 | 9/1984 | European Pat. Off. | 128/9272 |
| 2444831 | 9/1975 | Fed. Rep. of Germany | 623/18 |

*Primary Examiner*—Richard J. Apley
*Assistant Examiner*—David J. Isabella

[57] ABSTRACT

The present invention relates to a new and improved design for a device utilized as an interlocking femoral prosthesis under medical circumstances wherein either the femoral bone is fractured or there exists total hip failure requiring a hip replacement. By having the interlocking femoral prosthesis device be of an overall length, as in the case of a fracture, such that the lower portion of said device extends below the point of fracture of said femur and by utilizing three surgical screws for securing the interlocking femoral prosthesis within the femur canal, two of said screws passing distally through two elliptical holes formed within the interlocking femoral prosthesis, same being located below the fracture line of said femur when said device is implanted as related to a fracture situation and one of said screws passing proximally through one circular hole formed within the interlocking femoral prosthesis, at its upper portion which is positioned as in the case of a fracture, above the location of said fracture, when said device is implanted as related to a fracture situation, there is achieved the overall objects and advantages of the invention. Additionally, by having that portion of the device that is adjacent to the upper circular hole formed therein by of a porous construction, there is further achieved additional means for said device to anchor itself during the healing process to the femoral bone.

3 Claims, 1 Drawing Sheet

INTERLOCKING FEMORAL PROSTHESIS DEVICE

BACKGROUND AND OBJECTS OF THE INVENTION

In conjunction with present medical practice, prostheses devices have been known which are capable of implantation into the human femur either to medically address a fracture of the human femur or to achieve what has become known in medical practice as a hip replacement. Although medical techniques have existed utilizing prostheses implants which have in the past addressed such hip and femur problems, said prior art teachings, techniques and prostheses have a variety of drawbacks, both medically and physically, said prior art devices not addressing themselves to the various advantages inherent in the invention.

More particularly, it has been the common practice in the prior art in seeking to address a fracture of a human femur or as related to hip replacement to implant a hip prosthesis into said femur by driving said prosthesis into the femur canal and cementing said prosthesis in place with compounds capable of achieving the securing of said prosthesis within said femur. By so doing, there is necessitated in such a medical procedure surgical exposure of the fractured area so that the bone of the femur can be wired at the fracture site, same being required to prevent the cement compound from entering into the soft tissue area associated about the fracture site of the femur since said cement compound upon coming into contact with such soft tissue can cause damage to nerves, arteries, and veins. Additionally, said cement compounds have been found to prevent, impede and/or delay the healing process of said fracture site.

In conjunction with the above and upon review of the prior art to date, the following patents are representative of the prior art techniques referred to above, to wit, a patent issued to Bruce M. Cameron, U.S. Pat. No. 2,821,979, entitled INTRAMEDULLARY SPLINT; a patent issued to Ilias Konstantinou, U.S. Pat. No. 3,554,193, entitled FEMUR-SETTING SURGICAL DEVICE, a patent issued to Philip E. Getscher, U.S. Pat. No. 3,918,441, entitled INTRAMEDULLARY HIP PIN, a patent issued to Robert E. Zickel, U.S. Pat. No. 4,289,124, entitled SURGICAL APPLIANCE FOR THE FIXATION OF FRACTURED BONES, a patent issued to Onno Buning, et al, U.S. Pat. No. 4,404,691, entitled MODULAR PROSTHESIS ASSEMBLY, a patent issued to Hans G. Ender, U.S. Pat. No. 4,475,545, entitled BONE-NAIL and a patent issued to a Soviet Union inventor, Serial Number 104110-A.

In conjunction with the above and in keeping with the invention, it is, therefore, an object of the present invention to create a new and novel design for an interlocking femoral prosthesis device that overcomes the various problems and disadvantages inherent in the prior art device to date.

It is another object of the present invention to create a novel design for a device utilized as an interlocking femoral prosthesis wherein utilization of said device avoids the necessity of utilizing cementing compounds and the like for securing same upon implanting of same in said femoral bone.

It is another object of the present invention to create a novel design for a device utilized as an interlocking femoral prosthesis wherein the means for securing said device within the femoral bone is by utilization of pinning means that pass through elliptical openings formed in said device at the lower portion thereof.

It is another object of the present invention to create a novel design for a device utilized as an interlocking femoral prosthesis wherein the means for securing said device within the femoral bone is by utilization of pinning means that pass through a circular opening formed at the upper portion of said device.

It is another object of the present invention to create a novel design for a device utilized as an interlocking femoral prosthesis wherein the positioning of said pinning devices as they pass through said interlocking femoral prosthesis at the lower extremity of said device are such as to be distally positioned as related to said device and the patient involved while the positioning of said pinning devices as they pass through said interlocking femoral prosthesis at the upper portion thereof are proximally positioned as related to said device and the patient involved.

It is another object of the present invention to create a novel design for a device utilized as an interlocking femoral prosthesis wherein said device is capable of utilization with regard to allograft replacement of a portion of the femoral bone.

It is another object of the present invention to create a novel design for a device utilized as an interlocking femoral prosthesis wherein said device is capable of utilization with regard to tumor surgery as related to the femoral bone.

It is another object of the present invention to create a novel design for a device utilized as an interlocking femoral prosthesis wherein said device is capable of utilization with regard to total hip replacement.

It is another object of the present invention to create a novel design for a device utilized as an interlocking femoral prosthesis wherein the upper portion of said device adjacent to the circular opening formed therein is of a porous construction so as to enable during the healing process the adhering of bone tissue to said device.

The objects and advantages of the invention are set forth in part herein and in part will be obvious herefrom, or may be learned by practice of the invention, the same being realized and attained by means of instrumentalities and combinations printed out in the appended claims.

The invention consists in the novel parts, constructions, arrangements, combinations and improvements herein show and described.

SUMMARY OF THE INVENTION

The present invention relates to a new and improved design for a device utilized as an interlocking femoral prosthesis under medical circumstances wherein either the femoral bone is fractured or there exists total hip failure requiring a hip replacement. Upon the utilization of the present invention there is no longer needed the utilization of cement to achieve the implanting of said prosthesis into said femur canal. By having the interlocking femoral prosthesis device be of an overall length, as in the case of a fracture, such that the lower portion of said device extends below the point of fracture of said femur and by utilizing three surgical screws for securing the interlocking femoral prosthesis within the femur canal, two of said screws passing distally through two elliptical holes formed within the interlocking femoral prosthesis same being located below the fracture line of said femur when said device is implanted as related to a fracture situation and one of said screws passing proximally through one circular hole formed within the interlocking femoral prosthesis at its upper portion which is positioned as in the case of a fracture, above the location of said fracture, when said device is implanted as related to a fracture situation, there is achieved the overall objects and advantages of the invention. Additionally, by having that portion of the device that is adjacent to the upper circular hole formed therein be of a porous construction, there is further achieved additional means for said device to anchor itself during the healing process to the femoral bone.

The accompanying drawings referred to herein and constituting a part hereof are illustrative of the invention but not restrictive thereof, and, together with the description, serve to explain the principles of the invention.

DESCRIPTION OF A PREFERRED EMBODIMENT

Figure 1:
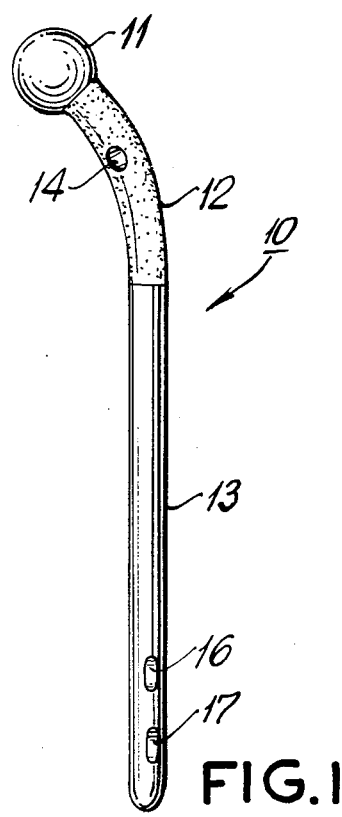
FIG. 1 is a three dimensional perspective view of an interlocking femoral prosthesis constructed in accordance with the invention.

Referring now more particularly to the embodiment of the above invention illustrated in the accompanying drawings, there is illustrated in FIG. 1 a three dimensional perspective view of an interlocking femoral prosthesis constructed in accordance with the invention, same being generally depicted by numerical designation 10.

Figure 2:
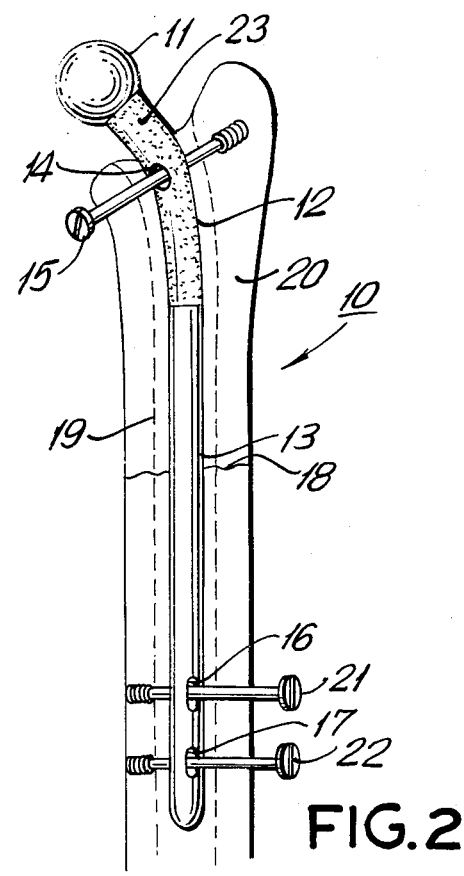
FIG. 2 is a cross-sectional view of the implantation of the interlocking femoral prosthesis depicted in FIG. 1 within the femoral bone in accordance with the invention.

Additionally, as set forth in FIG. 2, there is depicted a cross-sectional view of the implantation of interlocking femoral prosthesis 10 as depicted in FIG. 1 wherein interlocking femoral prosthesis 10 is implanted within the femoral cavity 19 of femur 20 in accordance with the invention.

As depicted in FIGS. 1 and 2, interlocking femoral prosthesis 10 is fashioned at its upper portion into a spherical shape member 11 capable of duplicating the human anatomy known as the femoral head. Additionally, the generalized configuration of interlocking femoral prosthesis 10 is such as to design a cylindrical neck member 12 that originates immediately below spherical shape member 11 whose axis defines an arch which then terminates in a blunted shaft member 13.

Inherent in the design of interlocking femoral prosthesis 10 and having same formed through cylindrical calcar member 12, is circular opening 14, aligned such that the axis of circular opening 14 passes through the center of cylindrical neck member 12 and is perpendicular to the arched axis of interlocking femoral prosthesis 10 at said location.

In keeping with the invention, circular opening 14 is capable of receiving the insertion therethrough of surgical screw 15, the positioning of the axis of circular opening 14 being such that upon implanting of interlocking femoral prosthesis 10 into the femur cavity of a patient, there results upon the insertion of surgical screw 15, the passing of same proximally through circular opening 14 thereby resulting in having surgical screw 15 pass through the femur.

In further keeping with the invention, elliptical openings 16 and 17 are formed through interlocking femoral prosthesis 10 at the location thereof designated as blunt shaft member 13, the orientation of the axis of elliptical openings 16 and 17 being at right angles to the axis of circular opening 14. By having said orientation as related to elliptical openings 16 and 17 be at right angles to the axis of circular opening 14, there is achieved, in accordance with the invention, the ability to pin by the use of surgical screws 21 and 22 respectively interlocking femoral prosthesis 10 without causing damage to the large muscle groups adjacent thereto.

As a result of having openings 16 and 17 formed in an elliptical shape while opening 14 is formed in a circular shape, as well as as a result of having interlocking femoral prosthesis 10 define an arch over a portion of its overall length, there is achieved, by the implantation of interlocking femoral prosthesis 10 in accordance with various medical procedures, the ability, when dealing with a fracture of the femoral bone, to avoid having said bone pull in opposite directions from the fracture point 18 thereof during a patient's movement, thereby impeding the healing process associated therewith.

It has been ascertained through prior medical observations and techniques that, by utilizing prior art prosthetic devices for implantation in the femoral canal which are pinned on opposite sides of the point of fracture within said bone, that stress occurs at the point of fracture during movement of a patient so treated such that the femoral bone and the soft tissue associated therewith on either side of said point of fracture pull in opposite directions from said point of fracture during certain movements of that portion of the patient's body, thereby impeding the healing process.

By utilizing elliptical openings 16 and 17 through which the pinning process is utilized in accordance with the present invention, there is avoided this situation, where, through the patient's movement of his body, there occurs a pulling away from said point of fracture of the opposite portions of said femoral bone since the elliptical openings through which said pinning occurs allows for a limited amount of movement of said adjacent soft tissue and the pin in question without causing a like movement of said interlocking femoral prosthesis 10.

In keeping with the invention, a variety of advantages are achieved by utilizing the present invention in conjunction with various medical problems associated with hip and/or femoral disorders.

In the first instance, the utilization of interlocking femoral prosthesis 10 in conjunction with FIG. 2 depicts its utilization in assisting in the medical treatment of a fracture of the femur bone, said fracture in said bone being designated by fracture line 18. In accordance with the invention, interlocking femoral prosthesis 10 is implanted into the femur canal 19 of femur 20 in accordance with well known medical practices, the positioning and overall length of interlocking femoral prosthesis 10 being such as to result in having eliptical opening 16 and eliptical opening 17 positioned below fracture line 18 of femur 20 while circular opening 14 is positioned above fracture line 18 of femur 20.

As depicted in FIG. 2 and in accordance with the invention, interlocking femoral prosthesis 10, upon implant, is oriented such that surgical screw 15 passes proximally through circular opening 14 while surgical screws 21 and 22 pass distally through elliptical openings 16 and 17 respectively. As a result, there is achieved the overall advantages and efficiencies of the invention enabling structural support to be imparted to femur 20 during the healing process.

In further keeping with the invention, and as depicted in FIG. 2, interlocking femoral prosthesis 10 has formed in FIG. 2 that portion of the device adjacent to circular hole opening 14 a porous structure at its surface location, same depicted generally by reference numeral 23. By there being formed at the surface of interlocking femoral prosthesis 10 said porous structure 23, there is provided a means whereby, during the mending process, the bone tissue adjacent thereto is able to adhere to and otherwise interreact in a mechanical structural relationship with porous structure 23 of interlocking femoral prosthesis 10, thereby creating an additional means for facilitating and otherwise achieving a medically sound technique for the mending and/or healing of a bone fracture of the femur bone.

Figure 3:
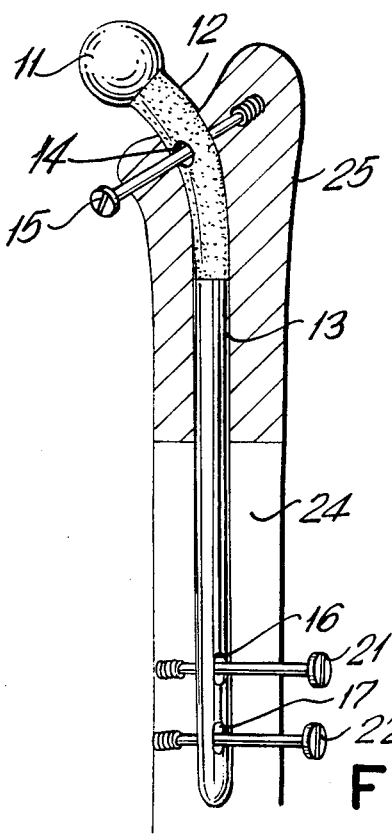
FIG. 3 is a cross-sectional view of the implantion of the interlocking femoral prosthesis as implanted in a femoral bone as utilized in an allograft procedure.

In FIG. 3, there is depicted the implanting of interlocking femoral prosthesis 10 into the femur canal of femur 24 wherein replacement of a portion of the femur bone by way of a bone graft has occurred, said medical process being commonly referred to as an allograft, is achieved.

As depicted in FIG. 3, and in accordance with the invention, femur 24 has bone graft member 25 aligned as therein depicted in accordance with known medical techniques related to the grafting of bones, said process being referred to as allograft, interlocking femoral prosthesis 10 being implanted as therein positioned similar to the method described above in accordance with FIG. 2, said procedure resulting in the providing by use of interlocking femoral prosthesis 10 of structural support between bone graft member 25 and femur 24 so as to enable, promote and otherwise achieve healing as related to the medical technique involved.

Figure 4:
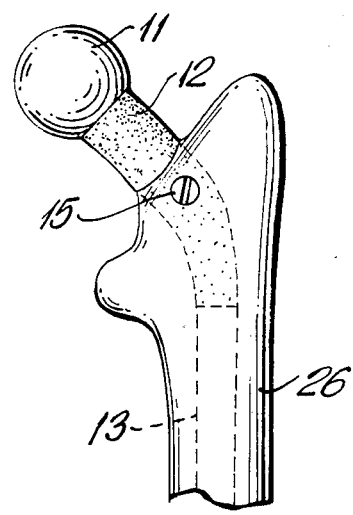
FIG. 4 is a cross-sectional view of the implantation of the interlocking femoral prosthesis as implanted in a femoral bone as utilized in tumor surgery.

In addition to the above, and as depicted in FIG. 4, interlocking femoral prosthesis 10 is capable of utilization in an implant capacity as regarding tumor surgery related to the femur bone.

As depicted in FIG. 4, a tumor appearing within the bone structure is surgically removed and in place thereof, there is implanted interlocking femoral prosthesis 10 similar to the discussion set forth above as regarding FIG. 2.

As depicted in FIG. 4, there is set forth an example of utilization of interlocking femoral prosthesis 10 as related to a tumor appearing on or in conjunction with the femoral head.

In keeping with the invention, it is within the scope thereof to utilize interlocking femoral prosthesis 10 in conjunction with tumors appearing in conjunction with the femur and/or the femoral head.

As stated above, FIG. 4 depicts the implantation of interlocking femoral prosthesis 10 into femur 26 after the surgical removal of the femoral head associated with femur 26 was necessitated due to the presence thereon of a tumor.

As indicated in FIG. 4, interlocking femoral prosthesis 10 is implanted in the same fashion and in accordance with the same procedures as set forth above as related to FIG. 2 and FIG. 3, the only difference being the circumstance which necessitated said implant.

In keeping with the invention and in accordance with sound medical practice, interlocking femoral prosthesis 10 in conjunction with the above procedures may possibly remain permanently implanted within the femur bone after implant once the healing process and the pins in question have been removed. Under such circumstances, interlocking femoral prosthesis 10 in effect becomes an inherent part of the bone structure at said location.

Additionally, it is within the scope of this invention for interlocking femoral prosthesis 10 to be utilized in accordance with the above discussion and as depicted in the drawings when a total hip replacement is necessitated due to medical circumstances.

The preceding description and accompanying drawings relate primarily to a specific embodiment of the invention, and the invention in its broader aspect should not be so limited to one specific embodiment as herein shown and described, but departures may be made therefrom within the scope of the accompanying claims without departing from the principals of the invention and without sacrificing its chief advantages.

I claim:

1. An interlocking femoral prosthesis capable of implanting within the human body, wherein said interlocking femoral prosthesis comprises:
    (a) a spherical shaped member structurally affixed to an arched cylindrical neck member, said arched cylindrical neck member being structurally affixed to a blunted shaft member, there being formed through said arched cylindrical neck member a singular circular opening, the axis of said circular opening passing through the center axis of said arched cylindrical shaft member there being formed through the lower portion of said blunted shaft member a first elliptical opening spaced from a second elliptical opening, said elliptical openings having the axis of each of said elliptical openings being parallel to each other and perpendicular to the axis of said circular opening;
    (b) a first screw member capable of insertion through said singular circular opening;
    (c) a second screw member capable of insertion through said first elliptical opening; and
    (d) a third screw member capable of insertion through said second elliptical opening.

2. An interlocking femoral prosthesis capable of implanting within the human body, wherein said interlocking femoral prosthesis is of unitary construction as described in claim 1 wherein said arched cylindrical neck member is of a porous structure about its surface.

3. The method of implanting an interlocking femoral prosthesis within the femur of the human body for purposes of assisting in the healing of a fracture thereof wherein said interlocking femoral prosthesis is of a unitary construction having formed at one end thereof a spherical shaped member structurally affixed to an arched cylindrical neck member, said arched cylindrical neck member being structurally affixed to a blunted shaft member, there being formed through said arched cylindrical neck member a singular circular opening, the axis of said circular opening passing through the center axis of said arched cylindrical shaft member and there being formed through the lower portion of said blunted shaft member a pair of spaced elliptical openings the axis of each said pair of spaced elliptical openings being parallel to each other and perpendicular to the axis of said circular opening, comprising the steps of:

(a) Inserting into the femoral canal of said blunted shaft member of said interlocking femoral prosthesis as well as said arched cylindrical neck member such that said pair of spaced elliptical openings formed through the lower portion of said blunted shaft member of said interlocking femoral prosthesis are located below the point of fracture of said femur while said singular circular opening formed through said arched cylindrical neck member of said interlocking femoral prosthesis occurs above said point of fracture of said femur;

(b) Aligning said interlocking femoral prosthesis about the vertical axis of said blunted shaft member of said interlocking femoral prosthesis such that the singular circular opening formed through said arched cylindrical neck member is capable of receiving a surgical screw therethrough such that said surgical screw passes through said arched cylindrical neck member of said interlocking femoral prosthesis proximally to said femur while said pair of spaced elliptical openings formed through said lower portion of said blunted shaft member of said interlocking femoral prosthesis are each capable of receiving a surgical screw therethrough such that each of said surgical screws pass through said blunted shaft member of said interlocking femoral prosthesis distally to said femur;

(c) Placing of a surgical screw through body tissue proximally to said femur and through said circular opening formed through said arched cylindrical neck member of said interlocking femoral prosthesis; and (d) Placing of a pair of surgical screws through body tissue distally to said femur and through each of said pair of spaced elliptical openings formed through said blunted shaft member of said interlocking femoral prosthesis.

* * * * *